(12) United States Patent
Fetz et al.

(10) Patent No.: US 9,283,152 B2
(45) Date of Patent: Mar. 15, 2016

(54) DENTAL COMPOSITION CONTAINING GLASS BEADS, PROCESS FOR PRODUCTION AND USE THEREOF

(76) Inventors: Johann Fetz, Windach (DE); Joachim W. Zech, Kaufering (DE)

( * ) Notice: Subject to any disclaimer, the term of this patent is extended or adjusted under 35 U.S.C. 154(b) by 0 days.

(21) Appl. No.: 12/681,269

(22) PCT Filed: Oct. 1, 2008

(86) PCT No.: PCT/US2008/078376
§ 371 (c)(1),
(2), (4) Date: Apr. 1, 2010

(87) PCT Pub. No.: WO2009/046056
PCT Pub. Date: Apr. 9, 2009

(65) Prior Publication Data
US 2010/0227946 A1    Sep. 9, 2010

(30) Foreign Application Priority Data

Oct. 4, 2007 (EP) .................................. 07117871

(51) Int. Cl.
*A61K 6/10* (2006.01)
*C08L 83/04* (2006.01)
*C08L 33/04* (2006.01)
*C08L 71/00* (2006.01)
*A61K 6/027* (2006.01)

(52) U.S. Cl.
CPC ................ *A61K 6/0276* (2013.01); *A61K 6/10* (2013.01)

(58) Field of Classification Search
None
See application file for complete search history.

(56) References Cited

U.S. PATENT DOCUMENTS

| | | | |
|---|---|---|---|
| 2,967,170 A * | 1/1961 | Merker | 528/15 |
| 3,539,530 A * | 11/1970 | Karstedt | 524/261 |
| 3,715,334 A | 2/1973 | Karstedt | |
| 3,775,352 A | 11/1973 | Leonard, Jr. | |
| 3,814,730 A | 6/1974 | Karstedt | |
| 3,933,712 A * | 1/1976 | Vanaglash, Jr. | 523/219 |
| 3,933,880 A | 1/1976 | Bergstrom et al. | |
| 4,035,453 A | 7/1977 | Hittmair et al. | |
| 4,273,902 A | 6/1981 | Tomioka et al. | |
| 4,394,465 A * | 7/1983 | Podszun et al. | 523/116 |
| 4,657,959 A | 4/1987 | Bryan et al. | |
| 4,672,081 A | 6/1987 | Fisher et al. | |
| 4,782,101 A | 11/1988 | Waller et al. | |
| 4,788,240 A | 11/1988 | Fujimoto | |
| 4,849,456 A * | 7/1989 | Champion | 521/54 |
| 5,202,362 A * | 4/1993 | Hermele | 523/218 |
| 5,204,362 A | 4/1993 | Seele et al. | |
| 5,249,862 A | 10/1993 | Herold et al. | |
| 5,286,105 A | 2/1994 | Herold et al. | |
| 5,332,122 A | 7/1994 | Herold et al. | |
| 5,464,131 A | 11/1995 | Keller | |
| 5,569,691 A | 10/1996 | Guggenberger et al. | |
| 5,612,066 A * | 3/1997 | Swenson | 425/425 |
| 5,684,060 A | 11/1997 | Konings et al. | |
| 5,750,589 A | 5/1998 | Zech et al. | |
| 5,776,399 A * | 7/1998 | Swenson | 264/219 |
| 5,924,600 A | 7/1999 | Keller | |
| 6,121,362 A * | 9/2000 | Wanek et al. | 524/448 |
| 6,135,631 A | 10/2000 | Keller | |
| 6,244,740 B1 | 6/2001 | Wagner et al. | |
| 6,313,190 B1 | 11/2001 | Bublewitz | |
| 6,486,237 B1 * | 11/2002 | Howe et al. | 524/71 |
| 6,555,056 B2 | 4/2003 | Nakagawa et al. | |
| 7,053,135 B2 | 5/2006 | Schaub et al. | |
| 7,287,898 B2 | 10/2007 | Pauser et al. | |
| 2003/0012967 A1* | 1/2003 | Janoff | 428/447 |
| 2004/0014907 A1 | 1/2004 | Nowak et al. | |
| 2005/0250871 A1 | 11/2005 | Bublewitz et al. | |

FOREIGN PATENT DOCUMENTS

| | | | |
|---|---|---|---|
| DE | 100 26 852 A1 | 12/2001 | |
| EP | 0 232 733 B1 | 10/1989 | |
| EP | 0 231 420 B1 | 9/1991 | |
| EP | 0 480 238 B1 | 7/1994 | |
| EP | 0 730 913 B1 | 10/2001 | |
| EP | 0 863 088 B2 | 12/2009 | |
| GB | 2 173 199 A | 10/1986 | |
| GB | 2173199 A * | 10/1986 | C08K 3/08 |
| JP | 2007-063389 | 3/2007 | |
| RU | 2 187 296 | 8/2002 | |
| WO | WO 97/40102 | 10/1997 | |

OTHER PUBLICATIONS

RTV615 High Strength Transparent Silicone Rubber Compound technical data sheet.*
International Search Report for PCT/US2008/078376.
Written Opinion for PCT/US2008/078376.
ISO 4823.
DIN 53504.
DIN 53505.

* cited by examiner

*Primary Examiner* — Peter A Salamon

(57) ABSTRACT

The invention relates to a dental impression composition comprising a hardenable matrix and glass beads having a particle size (d50/μm) equal or below about 60 μm. The invention also relates to a method of producing this composition and its use.

35 Claims, No Drawings

DENTAL COMPOSITION CONTAINING GLASS BEADS, PROCESS FOR PRODUCTION AND USE THEREOF

CROSS REFERENCE TO RELATED APPLICATIONS

This application is a national stage filing under 35 U.S.C. 371 of PCT/US2008/078376, filed Oct. 1, 2008, which claims priority to EP Application No. 07117871.9, filed Oct. 4, 2007, the disclosure of which is incorporated by reference in its/their entirety herein.

FIELD OF THE INVENTION

The invention relates to a dental composition containing glass beads and a process of production thereof. The dental composition can be used as a dental impression material.

BACKGROUND OF THE INVENTION

A widely used class of impression materials are alginates. Alginates consist of derivatives of alginic acid which, after stirring with water, cure in a sol-gel process. Typically, these impressions are made as so-called one-phase or monophase impressions, i.e. only a single viscosity of the impression material is employed when taking the impression. Alginate impression materials are also generally cheaper than many other impressions materials, such as vinyl polysiloxane (VPS) impression materials. Alginates are often used for study models, as a matrix for temporary crown and bridge materials, and for making orthodontic impressions. Due to their low tensile strength and elongation at break values, they are usually easy to cut or trim. This can be an advantage for some applications, e.g. in the orthodontic field. For example, materials with a comparable low tensile strength can facilitate making impressions over brackets of a patient receiving an orthodontic treatment without causing the risk of pulling off the brackets during removal of the set impression due to the low tear resistance at these spots.

Due to these features, alginates are often the material of choice for specific impressioning applications.

However, cured alginate impression materials typically lack dimensional stability due to loss of water and cannot be stored over a long period of time without degradation.

Also, for impressions that are used as a matrix for temporary crown and bridge (C&B) materials, it may be desirable for the material to have a low elongation-potential, that is, low elasticity. Generally, alginates are not very elastic.

Alginate impression materials are also sometimes cumbersome to be used. They have to be prepared freshly by mixing an alginate powder with water. Thus, they cannot be provided in ready-to-use foil bags.

Therefore specially designed VPS impression materials have been developed trying to mimic the properties of alginates but trying to keep the advantage of high dimensional stability of VPS impression materials combined with the ability to mix them in automatic mixing systems (Garant™ or Pentamix™; 3M ESPE). An example of such a dental composition is given in U.S. Pat. No. 6,121,362.

These materials are quite successful in the market (Position™, 3M ESPE), but they still show properties which are not identical to alginates, e.g. with regard to tensile strength and elongation at break.

A reduction of the physical strength of the set VPS material cannot be easily reached without jeopardizing other feature like curing speed, elastic recovery or shore hardness or prize.

Thus, there is a need for a substitute or alternative for alginate containing impression materials. There might also be a need for reducing efforts in the production process, packaging process or storage process.

RU 2 187 296 is directed to a silicone composition for formation of lining layers of removable dental prosthesis foundation containing an organosilicone rubber, metal oxides pigment, a catalyst, glass microspheres, polydimethylsiloxane and a surfactant-glycerol. The composition is useful in the area of stomatology. Moreover, it is stated that this composition is moisture resistant and shows and increased adhesion and strength. No hint to the particle size is given.

GB 2 173 199 describes a dental composite resin composition useful as a filling material for repairing a tooth cavity. It is mentioned that the composition can contain a variety of fillers such as quartz, glass beads, aluminium oxide and ceramics. As suitable particle size of the inorganic fillers a size of 50 µm or less is described.

U.S. Pat. No. 4,394,465 relates to a dental material based on organic plastics in paste form to be used as a dental filling material. The dental material can contain fillers such as glass beads having an average diameter of 5 to 80 µm.

SUMMARY OF THE INVENTION

It has been found that one or more of the above mentioned objectives can be addressed by providing a dental composition, especially a dental impression composition, comprising a hardenable matrix and glass beads having a particle size (d50/µm) equal or below about 60 µm.

The invention also relates to a dental composition comprising a) at least one organopolysiloxane with at least two pendant or terminal triorganosiloxy groups in which at least one of the three organic groups is a group with an ethylenically unsaturated double bond as component (A),
b) at least one organohydrogenpolysiloxane as component (B)
c) a catalyst as component (C),
d) glass beads as component (D), in an amount of about 0.1 to about 80 wt.-% with respect to the whole composition,
e) optionally at least one non-reactive polydimethylsiloxane as component (E),
f) optionally fillers as component (F), being different from the glass beads of component (D),
g) optionally surfactants as component (G) and
optionally further additives as component (H) selected from the group consisting of pigments, colorants, plastizers, inhibitors, hydrogen scavengers and mixtures of any of those.

The invention also relates to a process for producing the dental impression materials, the process comprising the step of adding glass beads to a hardenable matrix comprising components (A), (B) and (C) as mentioned in the description of the invention.

In another aspect, the invention relates to a kit of parts comprising a base part and a catalyst part separated from each other before use, wherein at least one part comprises glass beads.

In a further aspect, the invention relates to a process of using glass beads for the production of dental materials.

In another aspect the invention relates to a method of using the dental composition comprising glass beads as or for the preparation of impression materials or temporary or permanent crown and bridge materials.

In a further aspect, the invention relates to a method of using the dental composition comprising glass beads as a substitute for alginate.

DEFINITIONS

Within the description of the invention, the following terms are defined as follows:

A "hardenable matrix" may be described as the components of a composition contributing to the formation of a network due to chemical interaction (e.g. formation of chemical bondings) between the components thereby leading to a significant change in rheological properties like viscosity.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is carried out by placing a liquid material into the mouth in a customised tray. The material then sets to become an elastic solid, and when removed from the mouth retains the shape of the teeth. Common materials used for dental impressions are alginate, agar, polyethers including aziridino substituted polyether materials and silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

The term "glass" refers to an amorphous material having a glass transition temperature.

The term "amorphous material" refers to material derived from a melt and/or a vapour phase that lacks any long range crystal structure as determined by X-ray diffraction and/or has an exothermic peak corresponding to the crystallization of the amorphous material as determined by a DTA (differential thermal analysis).

The term "glass beads" means spherical beads comprising at least one amorphous, fused metal or non-metal oxide and having a smooth surface. The terms "beads" and "microspheres" are used interchangeably and refer to particles that are substantially, although perhaps not exactly, spherical. The term "solid" refers to beads that are not hollow, i.e., they lack substantial cavities or voids. Solid beads are typically more durable than hollow beads.

The term "essentially spherical" means including beads with natural variations from true spherical due to random fluctuations in formation processes.

"Hollow glass beads" refers to glass beads containing two phases, an outer solid phase made of glass surrounding an inner phase, which might be gaseous or contain vaccum. If the inner phase contains a gas, the gas is typically air or an inert substance like nitrogen or argon.

The mean particle size can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term d50/μm with regard to particle size measurement means that in 50% of the analyzed volume, the particles have a size below x μm. E.g., a particle size value of below 100 μm (d50/μm) means that within the analyzed volume, 50% of the particles have a size below 100 μm.

A "surfactant" is an agent imparting wettability to a material, that is making the material more wettable compared to a material not containing a surfactant. The wettability can be determined by the water contact angle which can be measured using e.g. a goniometer DSA 10 (Krüss). A low water contact angle indicates a better wettability.

"Setting time" is the time starting from the beginning of mixing the individual components until an elastomeric product is obtained (transition of the composition from a plastic into an elastic phase, characterized e.g. by strongly reduced flow capability)

More specifically, the setting time is the time between positioning of the spoon with the dental material in the mouth of the patient and removal of the cured material, and can also be called the mouth residence time or period. Setting times of <about 3 min mouth residence time, preferably <about 2.5 min, and particularly preferably <about 2 min are desirable properties for the dentist working with situation impression materials. For example, the one-phase impression material Imprint™ (3M ESPE) has a setting time of about 5 minutes, while a typical alginate impression material such as Palgat™ (3M ESPE) has a setting time of about 4 min.

The term "automixer-suitable impression material" relates to a multicomponent impression material which can be dispensed, for example, from a two-component disposable cartridge through a static mixer, e.g., of SulzerMixpac Company (U.S. Pat. No. 5,464,131, EP 0 730 913 A1) or from tubular film bags in dual-chamber reusable cartridges through a dynamic mixer, e.g., in the "Pentamix™" and "Pentamix™ 2" devices of 3M ESPE Company (U.S. Pat. Nos. 5,286,105 and 5,249,862).

By "paste" is meant a soft, viscous mass of solids dispersed in a liquid.

A "dental compositions and dental articles" within the meaning of the present invention is a composition which is to be used in the dental field (including restorative and prosthodontic work) including the orthodontic area. In this respect, a dental composition typically does not contain hazardous substances. Commercially available products have to fulfil certain requirements such as those given in ISO 4823. Typically, those compositions cure or set at ambient conditions.

A situation impression is an impression which is taken to record the starting situation of the hard and soft dental tissue (teeth and gingival) of the patient before the start of the preparation of one or more teeth.

By a temporary or long term crown and bridge material is meant a material, which is used for the preparation of dental crowns and bridges containing hardenable monomers, including (meth)arylates. These materials are typically used during the time period needed for making a permanent restoration. A typical time period ranges from a few days (e.g. 3 to 5) over weeks (1 to 3) to a few months (1 to 6). A long term crown and bridge material is typically used over a time period of about 6 to about 24 month.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF THE INVENTION

Using glass beads in dental compositions may help in influencing (e.g. reducing) the value of some physical parameters such as the mechanical strength of the network in a controlled way, sometimes even without sacrificing other important physical parameters such as setting time and/or consistency.

Without wishing to be bound by any theory, it is believed that the glass beads can act as a lubricant, probably due to the spherical shape of the glass beads (comparable to a ball bearing). This behaviour can be an advantage in some areas.

In the dental practice, comparable cheap impression materials, e.g. materials based on alginates are often employed for taking impressions of teeth and parts of the jaw for evaluation, diagnosis, planning and monitoring the accuracy of the fit of conservation, prosthetic and orthodontic work. In this procedure, there is no need for a highly precise impression. A rough form of the jaw and teeth is often considered sufficient and the form is recorded instantaneously by preparing a so-called situation impression.

After the situation impression has been filled with e.g. a gypsum suspension, the dentist then has a so-called study model, diagnostic model, documentation model or working and planning model. So-called counter-jaw models are also made to reproduce the opposite jaw for more extensive prosthetic work, and these are obtained by impressions with alginates.

Due to the physical features of the inventive composition, this composition can be used e.g. as a substitute for an alginate containing impression materials and may facilitate e.g. the taking of impressions of dental tissue, even if the hard tooth substance bears orthodontic appliances.

Another field of use for the inventive composition is the production of (provisional or temporary or long term) crowns and bridges. In this procedure, a situation impression which records the starting situation is taken on the patient before the start of the preparation of one or more teeth. After the preparation has taken place, a (provisional or temporary or long term) crown and bridge material, which is initially still in the pasty state, is incorporated at the appropriate points in the situation impression. This impression filled with the pasty material is then reset in the patient's mouth, where the crown and bridge material cures to form the (provisional) prosthesis.

It can be advantageous, if the material is easy to cut in the cured state, to influence shaping of the (provisional) prosthesis.

Thus, the inventive composition, if having reduced mechanical properties such as a low tensile strength, can also be used in the process for making (temporary) crown and bridges.

Another advantage can be seen in the reduced density, especially if hollow glass beads are used. Due to the low density of the hollow glass beads, the composition itself typically has also a reduced density compared to a composition containing usual fillers like silica, diatomaceous earth or quartz. This might help in reducing the efforts in the production process, the packaging process and storage.

In certain embodiments of the invention, the dental composition containing glass beads may show improved flowing properties. This might help in reducing the forces needed for delivering the composition out of cartridges, especially if a manually operated pre-filled dual cartridge dispenser with a static mixing tip is used. In certain embodiments an improvement in flow properties may also contribute to a reduction of the number of voids in the impressions which might be caused by an insufficient rheological behaviour. This can be true not only for alginate-like materials but also for other kind of impression materials including impression materials used for crown and bridge impression (elastomeric impression materials, irreversible elastomeric impression materials) and bite registrations.

Another advantage can be seen in the fact that cured dental composition according to the invention may be poured several times in spite of a possible reduced tensile strength. In contrast to this, impressions made with alginates usually can be poured only once. Due to loss of its dimensional stability the cured alginate impression typically becomes unsuitable during removal of the set plaster model from the impression.

The inventive composition contains a hardenable matrix.

The hardenable matrix may be comprised in the curable dental composition in an amount of about 1 to about 99 wt.-% or in an amount of about 10 to about 80 wt.-% or in an amount of about 20 to about 60 wt.-%.

The hardenable matrix can contain polyether, polyester, polyesters, polyacetals, polyurethane or polysiloxane moieties or a mixture of two or more of these moieties.

The curing of the hardenable matrix can be accomplished via a ring-opening polymerization reaction (including the ring-opening of aziridines) or via an addition or condensation polymerization reaction.

According to the invention, the dental compositions can generally comprise any multiplicity of types of compounds which, when mixed shortly before taking an impression, result in the formation of a rubber like impression material due to a polymerization reaction. Generally, polyaddition, ring-opening polymerization and polycondensation are preferred types of polymerization reactions, wherein polyaddition and ring-opening polymerization are sometimes preferred.

While the art of preparing dental materials knows many different types of compounds, a typical curing mechanism is based either on polycondensation reactions of alkoxy slilyl groups which might take place in the presence of an acidic catalyst or salt of a strong acid and water, or on polycondensation reactions of alkoxy slilyl groups with silanol groups in the presence of a catalyst without water or based upon the ring-opening polymerization e.g. of aziridines or based upon the polyaddition of silanes with olefinically unsaturated double bonds.

In one embodiment, polysiloxanes are comprised in the hardenable matrix of the inventive dental composition. Suitable polysiloxanes, which can be used, include those which meet the requirements needed during the preparation of dental materials.

A typical curing mechanism for this kind of substance is a polyaddition reaction of silane moieties and olefinically unsaturated double bonds in the presence of a catalyst, such as Pt containing compound.

Comprised are also alkoxyfunctionalized polyethers crosslinking via a condensation reaction as described in US 2005/250871.

It can also be preferred according to the invention, if the curing of the hardenable matrix can be effected by compounds with aziridino groups, e.g., aziridino groups being present in polyethers.

Appropriate polyethers can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

In certain embodiments polysiloxane carrying aziridino-groups as described in DE 100 26 852 A1 from p. 2, line 55 to p. 8, line 20 (corresponding to might be useful. The disclosure of this document is herewith incorporated by reference and regarded as part of the disclosure of the present text.

Moreover, all polymers which can be prepared by polycondensation methods are generally suitable in the context of the invention as polycondensation products.

Suitable polyesters, which can be used, include those obtainable by polycondensation of dicarboxylic acids with diols or by polycondensation of oxycarboxylic acids having a substantially linear structure.

The concomitant use of small amounts of tri- or tetra-functional alcohols or carboxylic acids during the polycondensation is possible and, in some cases, can even be advantageous for the mechanical properties of the compositions.

Polyacetals can also be suitable as polyol condensation products. Polyacetals are sometimes understood to be compounds obtainable by reacting glycols, e.g. diethylene glycol or hexanediol or a mixture thereof, with formaldehyde. Polyacetals, which can be used in the context of the invention, may also be obtained by the polymerisation of cyclic acetals.

Suitable polyaddition products, which can be used, include those which can be prepared by polyaddition methods provided that they meet the requirements of the composition with regard to the preferred use thereof as dental materials. Suitable polyaddition products are, for example, polyurethanes or polyethers.

Suitable polyurethanes, which can be used, include those which can be prepared by the reaction of polyols or polycarboxylic acids and isocyanates. Appropriate preparation methods are known to the person skilled in the art. Suitable polyols have already been described in the context of the present text as starting materials for the preparation of polyesters.

In the context of another embodiment of the invention, as constituents of the compositions polyaddition products, including polyethers can be used.

Suitable polyethers, which can be used, include those which meet the requirements in terms of material properties with regard to the preferred use as dental materials. Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

Depending on the purpose and formulation chosen, the inventive composition can contain glass beads in an amount of about 0.1 to about 80 wt.-% or an amount of about 0.5 to about 70 wt.-% with respect to the weight of the whole composition.

If hollow glass beads are used, the amount added might be smaller or shifted to the lower end of the above mentioned range. Suitable ranges include an amount of about 0.1 wt.-% to about 60 wt.-% or an amount of about 0.5 to about 55 wt.-% or an amount of about 1 to about 50 wt.-% with respect to the weight of the whole composition.

If solid glass beads are used, the amount added might be bigger or shifted to the upper end of the above mentioned range. Suitable ranges include amounts of about 0.2 to about 80 wt.-% or about 1 to about 70 wt.-% with respect to the whole composition.

If the dental composition contains only a minor amount of glass beads (e.g. below about 0.05 wt.-% with respect to the whole composition), the influence of the glass beads on the overall properties of the composition can usually be neglected.

If the dental composition contains a too high amount of glass beads (e.g. above 65 wt.-% or above about 70 wt.-% hollow glass beads with respect to the whole composition), the composition obtained might become too viscous and thus might be difficult to be dispensed out of e.g. cartridges. That is, the force needed to extrude the composition out of a container or cartridge might become unacceptable high. Moreover, it has sometimes been observed that it can be difficult to prepare a paste-like composition with sufficient homogeneity and flow properties.

Glass beads and microspheres which can be used in the present invention are known in the art and have been developed for and used in a variety of applications. E.g., glass beads have been used in retroreflective products and in optical devices. Beads for mechanical uses often contain significant amounts of alumina or zirconia.

Glass beads are generally made from, for example, high purity silica, active rare earth dopant, and modifying dopant precursors. Generally, the high purity silica precursor contains less than 1000 ppm of metal atoms or ions that are not silicon. In other embodiments, the high purity silica precursor contains less than 1000 ppm of metal atoms or ions that are not silicon and less than 100 ppm transition metals. In other embodiments, the high purity silica precursor contains less than 1000 ppm of metal atoms or ions that are not silicon and less than 1 ppm transition metals.

Useful silica precursors include alkoxysilanes, siloxanes, silicon halides, colloidal silica, soluble fluorosilicates, and mixtures thereof. Specific useful silica precursors include tetraethoxysilane, tetramethoxy silane, tetrapropoxysilane, tetrabutoxysilane, and silicon tetrachloride.

Spherical particles can be preferred since they are free flowing and conform readily to moulding cavities.

Glass beads, which can be used in the dental composition of the present invention, are available from 3M Company, Minnesota e.g. under the trade names 3M Glass Bubbles K1, K15, K20, K25, K37, K46, S22, S32LD, S32, S38, S38HS, S39, S60, S60H, S32LD or iM30K.

For a particular purpose the particles may be selected to be within a relatively narrow size range, i.e., substantially all of the particles having diameters + or −20 percent of the mean diameters. These glass beads are sometimes also be referred to as being substantially uniform However, because glass beads are sized by screening methods, the actual spread of diameters may be somewhat greater.

As used herein, "substantially uniform" means the spheroidal particles generally of such size range, but not containing many particles of much greater or much smaller diameter as these would tend to increase the packing density to an undesirable degree.

Preferably, glass beads to be used in the dental composition of the invention are functionally homogeneous. Generally, functionally homogeneous beads are substantially homogeneous. However, functionally homogeneous beads may have certain inhomogeneous features. For example, glass beads having a core region and a shell region of a different glass composition behave similarly to a homogeneous glass bead having the glass composition of the shell for applications and analyses where the light propagates primarily or exclusively in the shell region.

Generally, the glass beads can be solid spheres or hollow spheres. Depending on the intended use, the use of either of which or a mixture of both of which can be preferred.

The particle size can vary over a considerable amount. Glass beads which can be used according to the invention include glass beads having an absolute particle size of up to about 120 µm or up to about 100 µm or up to about 80 µm. There is no specific lower limit, however, useful glass beads can have a particle diameter as low as about 10 µm or about 20 µm or about 30 µm.

Glass beads having a mean particle size equal or below about 60 µm were found to be useful, especially for the production of alginate-like dental impression compositions. Typically, the d50/µm value of suitable glass beads is equal or below (≤) about 60 µm or equal or below about 55 µm or equal or below about 50 µm.

The particle size can be taken from the supplier specification. Means for the determination of the particle size and the distribution of particles are know to the expert. E.g. granulometers from CILAS Company can be used, which determine the particle size by a laser diffraction method.

The particle size and/or the particle size distribution of the glass beads can have an influence on the properties of the dental composition, especially with respect to homogeneity and the behaviour in the patient's mouth.

A dental composition containing glass beads having a huge mean particle size (e.g. above about 65 µm or above about 70 µm) may tend to generate a grinding or scratching feeling, whereas dental compositions containing glass beads having a smaller mean particle size tend to generate a more pleasant, creamy feeling, if used in the patient's mouth.

Moreover, an impression taken with a dental composition containing glass beads with a huge mean particle size might be less precise compared with a dental composition containing glass beads having a mean particle size of below about 65 µm. The precision of an impression can be determined e.g. visually or using a microscope or according to ISO 4823 (detail accuracy).

The density (bulk density) of the glass beads can vary over a considerable range as well. As an example, the density of hollow glass beads can be in a range of about 0.10 to about 0.70 g/cm$^3$ or in a range of about 0.15 to about 0.60 g/cm$^3$ or in a range of about 0.20 to about 0.50 g/cm$^3$. Typically, the bulk density of hollow glass beads is less than about 1 g/cm$^3$. For solid glass beads the density is usually higher e.g. above about 1 g/cm$^3$ or above about 1.2 g/cm$^3$.

The density can be determined by means know to the expert. For a homogeneous object, the formula mass/volume may be used. The mass is normally measured with an appropriate scale; the volume may be measured directly (from the geometry of the object) or by the displacement of a liquid (Archimedes method). A very common instrument for the direct measurement of the density of a liquid is a hydrometer.

The glass beads can also be characterized by their strength or crushing resistance and can vary over a considerable range, too.

Another parameter for characterizing especially hollow glass beads is the impact strength value. The impact strength value can be equal or above about 250 psi (corresponding to about ≥1.7 MPa), or equal or above about 1,500 psi (corresponding to about ≥10.3 MPa), or equal or above about 10,000 psi (corresponding to about 69 MPa) or equal or above about 20,000 psi (corresponding to about ≥137.9 MPa) or equal or above about 28,000 (corresponding to about ≥193 MPa).

The impact strength given above is taken from the manufactures instruction for use, but can also be determined also according to 3M QCM 14.1.8 as indicated in the respective product description.

According to one embodiment, the hardenable dental composition shows at least one of the following parameters:
- a consistency (according to ISO 4823) of 0 or 1 (corresponding to at most 35 mm) or 2 (corresponding to 31 mm to 41 mm) or 3 (corresponding to at least 36 mm), preferably 2; and/or
- a setting time within about 15 or about 10 or about 8 or about 6 or about 5 or about 4 min after mixing at ambient conditions (e.g. about 23° C.).

The setting time data can be measured using a Wallace-Shawbury Curometer (Croydon, GB). The Curometer measures the cure time of rubber and other cross linking polymers. It can also measure the setting time of resins, cements and dental impression and filling materials. The Curometer can be used for initial research into stock formulation and also for rapid evaluation of cure for quality control. The terms "cure" or "vulcanisation" usually refers to the change in a network molecular structure. The Curometer measures the times of beginning of cure and end of cure. The shape of the Curometer curve provides a picture of cure characteristic in which the "delay period" and rate of cure can be seen. The Curometer run time is started with the beginning of the mixing.

The end of the setting time is typically defined as the time after which the curing curve fells below the 10 mm line of the measuring tape.

According to another embodiment, the hardened or cured dental composition shows at least one of the following parameters:
- a tensile strength (according to DIN 53504) of about 0.1 to about 5 MPa or about 0.2 to about 3 MPa or 0.3 to about 1 MPa,
- an elongation at break (according to DIN 53 504) of about 10 to about 300% or about 15 to about 200%, or about 20 to about 100%,
- a shore A hardness (according to IN 53 505) of about 15 to about 75, or about 30 to about 50,
- a density (according to the Archimedes method; weight of 1 ml cured composition) of the composition of about 0.4 to about 1.8 g/ml or about 0.4 to about 1.0 g/ml.

A composition having a sufficient tensile strength and elongation at break as mentioned above can sometimes be desirable, especially, if the composition is to be used as a situation impression material or as a substitute for alginate.

According to another embodiment, the combination of a sufficient Shore A hardness and a low density of the composition can be desirable.

According to one embodiment, the invention features a dental composition comprising
- at least one polydimethylsiloxane with at least 2 aliphatically unsaturated groups as component (A),
- at least one SiH compound with ≥2 SiH-groups per molecule, as component (B),
- a catalyst as component (C) being able to catalyse the reaction between components (A) and (B),
- glass beads as component (D) in an amount of about 0.1 to about 80 wt.-% with respect to the weight of the whole composition,
- optionally at least one non-reactive polydimethylsiloxane as component (E),
- optionally fillers as component (F) being different from the glass beads,
- optionally surfactants or wetting agents as component (G), and
- optionally further additives as component (H) selected from the group consisting retarders, rheology modifiers, hydrogen absorbers, inhibitors, pigments, plasticizers, dyes, pigments, odorous substances, flavourings, hydrogen scavenger alone or in admixture.

With respect to this embodiment, the inventive composition contains as component (A) or as a part of component (A) an organopolysiloxane with at least two pendant or terminal triorganosiloxy groups in which at least one of the three organic groups is a group with an ethylenically unsaturated double bond. Generally, the groups with an ethylenically unsaturated double bond can be located on any monomeric unit of the organopolysiloxane. It is, however, preferred, that the groups with an ethylenically unsaturated double bond are located on or at least near the terminal, monomeric units of the polymer chain of the organopolysiloxane. In another embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula

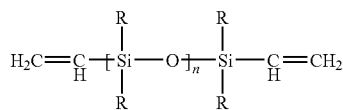

in which the radicals R, independently from each other, represent a non-substituted or substituted, monovalent hydrocarbon group with 1 to about 6 C atoms, which is preferably free from aliphatic multiple bonds and where n generally can be chosen such that the viscosity of the organopolysiloxanes lies between about 4 and about 1,000,000 mPas or between about 6 and about 500,000 or between about 10 and about 100,000 mPas. The parameter n can, e.g., be in the range of about 10 to about 10,000.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment of the invention, at least about 50% of the radicals R are methyl groups. Examples of other radicals R that can be present in the organopolysiloxanes according to the above formula are ethyl, propyl, isopropyl, n-butyl, tert.butyl, the pentyl isomers, the hexyl isomers, vinyl, propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is expressly regarded as being part of the disclosure of the present document and is included herein by reference.

The preparation of molecules according to the above-mentioned formula would generally be understood by the skilled person based upon the teachings of the prior art regarding similar molecules.

Particularly preferred are linear polydimethylsiloxanes according to the above formula having viscosities within the specified viscosity ranges and end groups comprising dimethylvinylsiloxy units and methyl groups as the radicals R.

A component (A) which can be employed according to the invention can consist of one type (A1) of organopolysiloxane. The organopolysiloxane can have a viscosity starting in the range of about 5 to about 1,000,000 mPas, or about 10 to about 500,000 mPas or about 20 to about 50,000 or about 30 to about 40,000 mPas.

It is, however, also possible that component (A) comprises two or more constituents, (A1), (A2) and so on, which can differ, e.g., in the chemical composition of their backbone, or their molecular weight, or their substituents or their viscosity, or any other differentiating feature or two or more of the above mentioned features.

In one embodiment of the invention the difference in viscosities of different constituents of component (A) can be higher than a factor of 2, e.g., higher than a factor of about 5, higher than a factor of about 10, higher than a factor of about 20, higher than a factor of about 30, higher than a factor of about 40, higher than a factor of about 50, higher than a factor of about 60, higher than a factor of about 70, higher than a factor of about 80, higher than a factor of about 90 or higher than a factor of about 100. The difference in viscosities can be even higher, e.g., higher than a factor of about 200, higher than a factor of about 300, higher than a factor of about 500, higher than a factor of about 800, higher than a factor of about 1,000 or higher than a factor of about 5,000, it should, however, preferably not exceed a value higher than a factor of about 10,000. It should be kept in mind that the values mentioned above relate to a factor for the difference in viscosities, not the viscosity values themselve.

The viscosity can be measured using a Haake Rotovisco RV20 device (spindle MV, measuring cup NV). The viscosity is typically measured at 23° C. After activation and rectification of the system, spindle MV is installed. Then the material to be measured is filled into the measuring cup NV. Without undue delay, the spindle is lowered into the measuring cup NV. The spindle should be covered by a layer of the material of a maximum thickness of 1 mm. The material to be measured is tempered for 20 min at 23° C. The measurement is started by starting the spindle to turn and the viscosity values (mPas) are recorded starting 20 s after the start of measurement. Care must be exercised to ensure that the measuring cup NV does not rotate or move at any time. A value for the viscosity is obtained in mPas. The above mentioned method of measurement corresponds to DIN 53018-1.

If component (A) contains constituents of different viscosities, the ratio of the amount of constituent with the lowest viscosity to the amount of constituent with the highest viscosity can be chosen relatively freely, depending on the desired properties of the precursors and the cured resin. It can, however, be advantageous when the ratio of the amount of constituent with the lowest viscosity to the amount of constituent with the highest viscosity is within a range of from about 1:20 to about 20:1, especially about 1:10 to about 10:1 or about 1:5 to about 5:1. Good results can e.g. be obtained with ratios of from about 1:3 to about 3:1 or about 1:2 to about 2:1. It can furthermore be adequate in some cases, when the amount of constituent with the highest viscosity is about equal to or higher than the amount of constituent with the lowest viscosity, resulting in a value of from about 0.9:1 to about 3:1 for the ratio of the amount of constituent with the highest viscosity to the amount of constituent with the lowest viscosity. All of the ratios are based on the weight of the constituents.

With respect to the above mentioned embodiment, the inventive composition contains as component (B) or as a part of component (B) an organohydrogenpolysiloxane with at least 3 Si-bonded hydrogen atoms per molecule. By definition, an organohydrogenpolysiloxane according to the present text does not belong to the group of organopolysiloxanes as described in the context of the invention.

An organohydrogenpolysiloxane according to the invention typically contains about 0.01 to about 1.7 wt.-% silicon-bonded hydrogen or about 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least about 50%, preferably about 100%, of the hydrocarbon radicals R that are bonded to silicon atoms are methyl radicals.

Organohydrogenpolysiloxanes which can be suitable as component (B) can have a viscosity of about 10 to about 1,000 mPas or from about 15 to about 550 mPas or from about 20 to about 150 mPas.

With respect to the above mentioned embodiment, the inventive composition also contains a catalyst as component (C) or as a part of component (C). This catalyst is typically a platinum catalyst or a platinum containing catalyst, including a platinum complex which can be prepared from hexachloroplatinum acid by reduction with tetramethyldivinyldisiloxane. Such compounds are known to the skilled person. Any other platinum compounds which catalyze or accelerate addition cross-linking of silanes with ethylenically unsaturated double bonds are also suitable. Platinum-siloxane complexes as described, e.g. in U.S. Pat. Nos. 3,715,334, 3,775,352 and 3,814,730 are suitable. The disclosure of these patents with regard to platinum complexes and their preparation is explicitly mentioned and expressly regarded as part of the disclosure of the present text.

The catalyst can typically be used in an amount of about 0.00005 to about 0.05 wt.-%, particularly about 0.0002 to about 0.04 wt.-%, each calculated as elemental platinum and related to the overall weight of the composition.

With respect to the above mentioned embodiment, the inventive composition also contains glass beads as component (D) or as a part of component (D), glass beads as described in the text of the invention.

Suitable compounds for use as component (E) or for us as part of component (E), with respect to the above mentioned embodiment, include organopolysiloxanes without reactive substituents. Non-reactive substituents include those which do not co-polymerize with the other components of the composition during the hardening process. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, $C_2$-$C_{10}$ aliphatics, trifluoropropyl groups as well as aromatic $C_6$-$C_{12}$ radicals.

Polydimethylsiloxanes with trimethylsiloxy end groups are particularly preferred as a constituent of component (E). Component (E) can be used in an amount of about 0 to about 40 wt.-%, or about 0.1 to about 20 wt.-% or about 0.5 to about 10 wt.-%.

Generally, the inventive composition may contain a filler or a mixture of fillers, e.g. as component (F) or as a part of component (F). The nature of the filler is not particularly limited, either. However, the filler, e.g. if used as component (F) with respect to the above mentioned embodiment, is different in its physical and/or chemical nature from the glass beads (e.g. used as component (D) with respect to the above mentioned embodiment).

Typically, filler can be used in an amount of from of at least about 15 wt.-% or at least about 20 or at least about 30 wt.-% with respect to the whole composition.

There is no particular upper limit, however, typically the amount of filler, if present at all, is used in an amount of at most about 70 wt.-% or at most about 60 wt.-% or at most about 50 wt.-% with respect to the whole composition.

Thus, typical ranges for the filler as component (F) are from about 15 to about 70 or from about 20 to about 60 or from about 30 to about 50 wt.-% with respect to the whole composition.

A wide variety of inorganic, hydrophilic or hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4-6 μm); amorphous silicone dioxides, such as a diatomaceous earth (4-7 μm); and silanated fumed silica, such as Cab-o-Sil TS-530 (160-240 m²/g), manufactured by Cabot Corporation.

The sizes and surface areas of the foregoing materials can be adjusted to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or alkoxysilanes or silazanes. Such fillers can be present in amounts of from about 0 to about 65% by weight, especially about 5 to about 55 or about 20 to about 50 wt.-% of the material.

Among the fillers which can be used are fillers such as quartz (density 2.65 g/cm$^3$), cristobalite (density 2.35 g/cm$^3$), calcium silicate, diatomaceous earth (density 2.2 g/cm$^3$), zirconium silicate, montmorillonite such as bentonite, zeolite, including molecular sieves such as sodium aluminium silicate (density: 2.61 g/cm$^3$ for Nephelinsyenit), metal oxide powder such as aluminium or zinc oxide (density 3.9 g/cm$^3$ for alumina) or their mixed oxides, barium sulphate, calcium carbonate, plaster, glass and plastic powder.

Suitable fillers are also pyrogenic or precipitated silicic acid and silica aluminium mixed oxides. Those filler are commercially available from companies like Wacker or Degussa under the trade names Aerosil™, HDK-H (density: 2.2 g/cm$^3$ for HDK-H 2000).

The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 µm.

A combination of reinforcing and non-reinforcing fillers can be preferred. In this respect, the quantity of reinforcing fillers can range from about 1 to about 10 wt.-%, in particular from about 2 to about 5 wt.-% with respect to the whole composition.

Typical reinforcing fillers include fumed silica, carbon black and the like. They also can be surface treated and can improve mechanical properties like tensile strength or tear strength, of the cured silicone composition.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Preferred non-reinforcing fillers are quartzes, cristobalites and sodium aluminium silicates which can be surface-treated. The surface treatment can generally be carried out with the same methods as described in the case of the strengthening fillers.

Typical non-reinforcing fillers are quartz, precipitated silicas, diatomaceous earth, aluminas, magnesias, titanium dioxide, zirconium silicate, metallic oxides, and the like. These fillers can be surface treated, e.g. silanated, or non surface treated. Typical particle sizes are about 2 to about 10 µm.

Surfactants or hydrophilizing agents which can be employed e.g. as component (G) or part of component (G) with respect to the above mentioned embodiment, can generally be chosen freely from all types of surfactants which improve the hydrophilicity of a silicone material which is curable via hydrosilylation reaction while at the same time do not negatively impact the material properties or curing behaviour of the material or at least not more than avoidable or tolerable. Useful surfactants which improve the hydrophilicity of a silicone material according to the invention can generally be chosen from anionic, cationic or non-ionic surfactants or mixtures of two or more of such types of surfactants.

It can be preferred that the material according to the invention comprises a nonionic surfactant as a hydrophilizing agent or a mixture of two or more non-ionic surfactants.

Component (G) can comprise an agent or a plurality of agents which are generally capable of increasing the hydrophilic character to a composition, for example as demonstrated by an increase in the wetting angle of a drop of water or an aqueous solution or dispersion (e.g. a plaster suspension or the like) on the material (in its cured or uncured state) over that wetting angle achieved on the same silicon composition without component (G).

A method for measurement of the wetting angle to determine the hydrophilicity of impression materials is described e.g. in U.S. Pat. No. 5,569,691, the contents of this document with regard to this method of measurement being expressly mentioned by reference and being regarded as part of the disclosure of the present text.

In certain embodiments, the surfactant does not contain reactive groups so that it is not incorporated into the polysiloxane network.

Ethoxylized fatty alcohols which are e.g. described in EP 0 480 238 B1 can be used. Furthermore, the non-ionic perfluoralkylated surface-active substances described in U.S. Pat. No. 4,657,959 can be used. Also preferred are the non-ionic surface-active substances which are described in U.S. Pat. No. 4,782,101, i.e. the nonylphenolethoxylates, polyethylene glycol-mono- and diesters, sorbitan esters as well as polyethylene glycol-mono- and diethers listed therein. The contents of the latter documents with regard to hydrophilizing agents and their preparation is expressly mentioned by reference and is regarded as part of the disclosure of the invention.

In a further embodiment of the invention, the surfactant or at least one of the surfactants, if component (G) comprises two or more surfactants, may contain silicone moieties.

Suitable hydrophilizing agents can be wetting agents from the group of hydrophilic silicone oils which are not capable of being covalently incorporated into the hardened polymer network. Suitable hydrophilizing agents are described in U.S. Pat. No. 4,657,959 and in EP 0 231 420 B1, the contents of which with regard to the hydrophilizing agents are expressly mentioned by reference and are regarded as part of the disclosure of the invention.

Useful surfactants include polyether carbosilanes of the general formula Q-P—(OC$_n$H$_{2n}$)$_x$—OT, in which Q stands for R$_3$—Si— or $$R_3—Si—(R'—SiR_2)_a—R'—SiR''_2,$$

where every R in the molecule can be the same or different and stands for an aliphatic C$_1$-C$_{18}$, a cycloaliphatic C$_6$-C$_{12}$ or an aromatic C$_6$-C$_{12}$ hydrocarbon radical, which can optionally be substituted by halogen atoms, R' is a C$_1$-C$_{14}$ alkylene group, R" is R in the case of a≠0 or is R or R$_3$SiR' in the case of a=0, and a=0-2; P stands for a C$_2$-C$_{18}$ alkylene group, preferably a C$_2$-C$_{14}$ alkylene group or A-R''', where A represents a C$_2$-C$_{18}$ alkylene group and R''' a functional group from the following list: —NHC(O)—, —NHC(O)—(CH2)$_{n-1}$-, —NHC(O)C(O)—, —NHC(O)(CH2)$_v$C(O)—, —OC(O)—, —OC(O)—(CH2)$_{n-1}$—, —OC(O)C(O)—, —OC(O)(CH$_2$)$_v$C(O)—, —OCH$_2$CH(OH)CH$_2$OC(O)(CH2)$_{n-1}$—, —OCH$_2$CH(OH)CH$_2$OC(O)(CH2)$_v$C(O)— with v=1-12; T is H or stands for a C$_1$-C$_4$ alkyl radical or a C$_1$-C$_4$ acyl radical; x stands for a number from 1 to 200 and n stands for an average number from 1 to 6, preferably 1 to 4.

The polyether part can be a homopolymer, but can also be a statistical, alternating or block copolymer.

Surfactants which can also be used, either alone or as a mixture of two or more thereof, can be found U.S. Pat. No. 5,750,589 (Zech et al), col. 2, l. 47 to col. 3 l. 27 and col. 3, l. 49 to col. 4, l. 4 and col. 5, l. 7 to col. 14, l. 20.

Other surfactants which can be used, either alone or as a mixture of two or more thereof, can be found in U.S. Pat. No. 4,657,959 (Bryan et al.), col. 4, l. 46 to col. 6, l. 52 as well as in EP 0 231 420 B1 (Gribi et al.) p 4, l. 1 to p. 5, l. 16 and in the examples.

U.S. Pat. Nos. 5,750,589, 4,657,959 and EP 0 231 420 B1 are expressly described and cited herein as a source of disclosure for compounds which can be used as component (G) according to the invention. The documents and especially their disclosure with regard to hydrophilizers at the citations given above are incorporated by reference and are considered as being a part of the disclosure of the present text.

Further preferred surfactants are exthoxylated surfactants containing a siloxane solubilizing group as described in U.S. Pat. No. 4,657,959, the disclosure of which is incorporated herein by reference.

Some of the surfactants can be summarized under the following formula

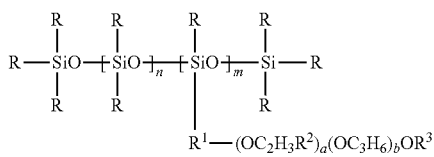

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is about zero or about one, m is about one to about five, a is about five to about 20 and b is about 0.

Several of such ethoxylated surfactants are available from Union Carbide Corp. as "SILWET" surface active copolymers. Preferred surface active copolymers include SILWET 35, SILWET L-77, L-7600 and L-7602. SILWET L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL® SF19, as obtainable from Lubrizol performance products, Spartanburg, US.

Also possible is the use of polyether carbosilanes selected from the group consisting of:
$Et_3Si$—$(CH_2)_3$—O—$(C_2H_4O)y$-$CH_3$, Et=Ethyl
$Et_3Si$—$CH_2$—$CH_2$—O—$(C_2H_4O)y$-$CH_3$, Et=Ethyl
$(Me_3Si$—$CH_2)_3Si$—$(CH_2)_3$—O—$(C_2H_4O)y$-$CH_3$, Me=Methyl
$Me_3Si$—$CH_2$—$SiMe_2$-$(CH_2)_3$—O—$(C_2H_4O)y$-$CH_3$, Me=Methyl
$(Me_3Si$—$CH_2)_2SiMe$-$(CH_2)_3$—O—$(C_2H_4O)y$-$CH_3$, Me=Methyl
$Me_3Si$—$(CH_2)_3$—O—$(C_2H_4O)y$-$CH_3$, Me=Methyl
$Me_3Si$—$CH_2$—$CH_2$—O—$(C_2H_4O)y$-$CH_3$, Me=Methyl
$Ph_3Si$—$(CH_2)_3$—O—$(C_2H_4O)y$-$CH_3$, Ph=phenyl
$Ph_3Si$—$CH_2$—$CH_2$—O—$(C_2H_4O)y$-$CH_3$, Ph=phenyl
$Cy_3Si$—$(CH_2)_3$—O—$(C_2H_4O)y$-$CH_3$, Cy=cyclohexyl
$Cy_3Si$—$CH_2$—$CH_2$—O—$(C_2H_4O)y$-$CH_3$, Cy=cyclohexyl
$(C_6H_{13})_3Si$—$(CH_2)_3$—O—$(C_2H_4O)y$-$CH_3$
$(C_6H_{13})_3Si$—$CH_2$—$CH_2$—O—$(C_4H_4O)y$-$CH_3$ in which y conforms to the relations: $5 \leq y \leq 20$.

Surfactants can be present in the inventive composition in an amount of more than about 0.1% by weight, relating to the weight of the whole composition. It can be preferred if the amount of surfactant as part of component (G) is in a range of from about 0.1 to about 15% by weight or from about 0.3 to about 12% by weight or from about 0.5 to about 8% by weight or from about 0.8 to about 7% by weight or from about 1 to about 6% by weight or from about 1.2 to about 5% by weight or from about 1.5 to about 4% by weight.

The wetting angle of a drop of water on the surface of a cured material according to the invention measured after 10 seconds, is preferably less than about 40° or less than about 20° or less than about 10° or even less than about 5°.

Wetting contact angles can be measured as follows: About 2.5 g of base and 2.5 g of catalyst paste are mixed together until uniform (about 30 s). 5 g of mixed paste is placed in a metal mould (40 mm×30 mm×2 mm) between two sheets of polyethylene and pressed flat using a glass plate. The specimen is allowed to stand undisturbed until set (about 15 minutes). The polyethylene sheets are removed, being careful not to touch the surface of the specimen, and the specimen placed on the table of a goniometer DSA 10 (Krüss), a well known device for measuring contact angles. 5 μl of water are placed onto the surface of the specimen and an automatic contact angle measurement is started using standard software of the goniometer. Measuring time is at least about 10 s up to about 200 s.

The inventive composition can also contain other additives e.g. as component (H) or part of component (H) with respect to the above mentioned composition, including retarders to modify the working and setting time, rheology modifiers, inhibitors, pigments, plasticizers (including paraffin oil or mineral oil), dyes, pigments, odorous substances, flavourings or hydrogen scavenger etc. alone or in admixture.

The additive(s) can be present in an amount in the range of about 0.05 to about 90 wt.-%, or in the range of about 0.1 to about 40 wt.-% with respect to the cured composition.

To control the reactivity of the addition reaction and to prevent premature curing, it may be advantageous to add an inhibitor which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the invention. Examples of such inhibitors include acetylenic unsaturated alcohols such as 3-methyl-l-butyne-3-ol, 1-ethynylcyclohexane-l-ol, 3,5-dimethyl-l-hexyne-3-ol and 3-methyl-l-pentyne-3-ol. Examples of inhibitors based an vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups.

The composition may also contain a component useful for diminishing the presence or degree of hydrogen outgassing which may be typically generated as a result of the vinyl polymerization. The composition thus may comprise a hydrogen scavenger such as finely divided platinum metal that scavenges for and takes up such hydrogen. The Pt metal may be deposited upon a substantially insoluble salt having a surface area of between about 0.1 and about 40 m²/g. Suitable salts include barium sulphate, barium carbonate and calcium carbonate of suitable particle sizes. Other substrates include diatomaceous earth, activated alumina, activated carbon and others. The inorganic salts may be preferred to imply improved stability to the resulting materials incorporating them. Dispersed upon the salts may be about 0.2 to about 2 parts per million of platinum metal, based upon the weight of the catalyst component. It has been found that employment of the platinum metal dispersed upon inorganic salt particles substantially eliminates or diminishes hydrogen out-gassing during curing of silicone containing compositions. Also Pd metal as described e.g. in U.S. Pat. No. 4,273,902 or Pd compounds as disclosed in to U.S. Pat. No. 5,684,060 can be employed.

A typical composition according to one embodiment of the invention can comprise the individual components in the following amounts:

Component (A): from about 20 wt.-% to about 60 wt.-% or from about 25 wt.-% to about 55 wt.-% or from about 36 wt.-% to about 53 wt.-% with respect to the whole composition.

Component (B): from about 0.1 wt.-% to about 15 wt.-% or from about 1 wt.-% to about 10 wt.-% or from about 3 wt.-% to about 5 wt.-% with respect to the whole composition.

Component (C): from about 0.001 wt.-% to about 0.1 wt.-% or from about 0.002 wt.-% to about 0.02 wt.-% or from about 0.005 wt.-% to about 0.01 wt.-% with respect to the whole composition.

Component (D): from about 1 wt.-% to about 70 wt.-% or from about 5 wt.-% to about 60 wt.-% or from about 25 wt.-% to about 50 wt.-% with respect to the whole composition.

Component (E): from about 0 wt.-% to about 30 wt.-% or from about 5 wt.-% to about 25 wt.-% or from about 10 wt.-% to about 20 wt.-% with respect to the whole composition.

Component (F): from about 0 wt.-% to about 70 wt.-% or from about 0.1 wt.-% to about 50 wt.-% or from about 0.5 wt.-% to about 40 wt.-% with respect to the whole composition.

Component (G): from about 0 wt.-% to about 10 wt.-% or from about 0.1 wt.-% to about 5 wt.-% or from about 0.2 wt.-% to about 2 wt.-% with respect to the whole composition.

Component (H): from about 0 wt.-% to about 10 wt.-% or from about 0.1 wt.-% to about 5 wt.-% or from about 0.2 wt.-% to about 2 wt.-% with respect to the whole composition.

The dental compositions according to the invention are typically multi component materials which comprise at least a curable base paste and a catalyst paste comprising a catalyst for curing at least part of the material of the base paste.

The components of the composition can be included in a kit, where the contents of the composition are packaged to allow for storage of the components until they are needed. When used, the components of the compositions can be mixed in the suitable amounts and clinically applied using conventional techniques.

Thus, the invention also relates to a kit of parts, comprising a base part (I) and a catalyst part (II) separated from each other before use, wherein the base part (I) comprises components (A) and (B), and the catalyst part (II) comprises component (C) or (C) and (A), and wherein component (D) is present either in the base part or the catalyst part or in the base part and the catalyst part. The other optional components (E), (F), (G), and (H) can be present in the base part or the catalyst part or in the base part and the catalyst part.

The volume ratios of catalyst paste and base paste can range from about 10:1 to about 1:10. Particularly preferred volume ratios of base paste to catalyst paste are about 1:1 and about 5:1 (5 parts of base paste to 1 part of catalyst paste).

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. Nos. 5,924,600, 6,135,631 or EP 0 863 088 A1 together with a dynamic mixing tip as mentioned in US 2004/0085854 or U.S. Pat. No. 6,244,740.

A further improvement of the handling properties of dental compositions can be seen in using an automatic mixing and metering systems for two-component compositions which have automatic conveying and mixing units, such as described e.g. in U.S. Pat. Nos. 5,249,862, 5,286,105 or 5,332,122. The result after mixing the respective pastes is usually a homogeneous product which is essentially free of air bubbles. Commercially available mixing devices are distributed by 3M ESPE under the brand Pentamix™ or Pentamix™ 2.

In practice, the impression material can be syringed through a static or mechanical mixing device into an impression tray or onto patient's teeth or tissue and placed in the patient's mouth. After the impression material is set, the tray is typically removed from the patient's mouth and, in instances where the dental practitioner prepares a positive model, it may be desirable to pour the negative model e.g., with plaster.

The invention also relates to a method of producing a curable composition comprising the step of combining glass beads with a hardenable matrix or a composition comprising components (A), (B), (C), wherein components (A), (B) and (C) are as described in the text of the invention.

Typically, after combining the class beads with the hardenable matrix or the individual components of the hardenable matrix, the components are mixed.

The invention also relates to a method of using glass beads for the production of a dental composition, wherein the glass beads are present in an amount of about 0.1 to about 80 wt.-% in the dental composition. Typically, the glass beads have a particle size (d50/μm) equal or below about 60 μm.

The dental material or composition can be used as or for the production of impression materials, (temporary or long term) crown and/or bridge materials. In the latter case, the inventive composition is used as a mould to be filled with the (temporary or long term) crown and/or bridge material, which is typically based on polymerizable (meth)acrylates.

The invention also features a method of using the dental composition described in the present text as a substitute for alginate, especially alginate impression materials.

With respect to a certain embodiment, the inventive dental composition does not necessarily comprise organo titanium components. According to another embodiment, there is also no need for organopolysiloxane oligomer to be present, wherein the ends of the molecular chain of the oligomer are blocked with diorganohydroxysilyl groups.

Features and advantages of this invention are further illustrated by the following examples, which are in no way intended to be limiting thereof. The particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Measurements

Tensile Strength

The tensile strength of the compositions were determined according to DIN 53504 and are given in MPa. Tensile strength data were evaluated by tearing six I-shaped specimens with a central unit of 20 mm×4 mm×2 mm in a Zwick 1435 Universal testing machine. Base and catalyst pastes were mixed through a static mixer and filled into a brass mould. After 24 hours at 23° C. the specimen were removed, six measurements were made and the mean value determined (speed 200 mm/min).

Consistency

The consistency of the compositions was determined according to ISO 4823 and is given in mm.

Shore A Hardness

The Shore A hardness of the compositions 24 h after mixing of the base and catalyst paste was determined according to DIN 53 505.

Density and Particle Size

The density (bulk density) and the particle size of the glass bubbles were taken from the respective product specification.

The following components or compositions were used (Table 1):

TABLE 1

| Component | Description | Availability |
|---|---|---|
| Express ™ 2 Light Body Flow | VPS composition | 3M ESPE Comp. |
| Position ™ Penta | VPS composition | 3M ESPE Comp. |
| Palgat ™ Plus Quick | Alginate impression material | 3M ESPE Comp. |
| Vinyl-terminated polydimethylsiloxanes (mixture) | Viscosity: 200 mPas or 2,000 mPas | Gelest Comp. |
| Silwet L-77 | Surfactant | Witco Comp. |
| Silicone oil | 50 mPas | |
| Silbond | Quartz (filler); hydrophobized | Quartz Werke |
| Aerosil | Pyrogenic silica (filler); hydrophobized | Degussa Comp. |
| Platinum - solution | Pt-Catalyst in silicone oil, 1 wt.-% Pt | |
| K37 | glass beads; d50/μm: 40 | 3M Comp. |
| iM 30 K | glass beads; d50/μm: <30 | 3M Comp. |
| Poly(methyl)(hydrogen)siloxane | 200 mPas | Gelest Comp. |

General Description of Production

The individual components of the base paste and the catalyst paste were mixed in the respective amounts using a laboratory mixer under vacuum and filled in a dual barrel cartridge (SulzerMixpac Company), volume ration 1:1, equipped with a static mixing tip (SulzerMixpac Company).

Example 1

| Component | Base paste (wt.-%) | Catalyst (wt.-%) |
|---|---|---|
| Vinyl-terminated polydimethysiloxane | 36.5 | 44.2 |
| Pigment | 2.0 | — |
| Surfactant | 0.9 | — |
| Silicone oil | 12.7 | 13.3 |
| Poly(methyl)(hydrogen)siloxane | 7.1 | — |
| Pyrogenic silica | 0.7 | 0.9 |
| Glass Beads (iM 30K), d50/μm: <30 μm | 40.1 | 40.6 |
| Platinum - solution | — | 1.0 |

Example 2

| Component | Base paste (wt.-%) | Catalyst (wt.-%) |
|---|---|---|
| Vinyl-terminated polydimethysiloxane | 36.5 | 44.2 |
| Pigment paste blue | 2.0 | — |
| Surfactant | 0.8 | — |
| Silicone oil | 12.7 | 13.3 |
| Poly(methyl)(hydrogen)siloxane | 7.1 | — |
| Pyrogenic silica | 0.6 | 0.9 |
| Quartz | 20.1 | 20.3 |
| Glass Beads (iM 30K), d50/μm: <30 μm | 20.2 | 20.3 |
| Platinum - solution | — | 1.0 |

Example 3

| Component | Base paste (wt.-%) | Catalyst (wt.-%) |
|---|---|---|
| Vinyl-terminated polydimethysiloxane | 36.5 | 44.2 |
| Pigment paste blue | 2.0 | — |
| Surfactant | 0.9 | — |
| Silicone oil | 12.7 | 13.3 |
| Poly(methyl)(hydrogen)siloxane | 7.1 | — |
| Pyrogenic silica | 0.7 | 0.9 |
| Quartz | 35.1 | 35.4 |
| Glass Beads (iM 30K), d50/μm: <30 μm | 5.0 | 5.2 |
| Platinum - solution | — | 1.0 |

Example 4

| Component | Base paste (wt.-%) | Catalyst (wt.-%) |
|---|---|---|
| Vinyl-terminated polydimethysiloxane | 33.6 | 40.9 |
| Pigment | 1.8 | — |
| Surfactant | 0.9 | — |
| Silicone oil | 11.5 | 12.0 |
| Poly(methyl)(hydrogen)siloxane | 6.5 | — |
| Pyrogenic Silica (Aerosil R 202) | 0.6 | 0.8 |
| Glass Beads (iM 30K), d50/μm: <30 μm | 45.1 | 45.3 |
| Platinum - solution | — | 1.0 |

Example 5

| Component | Base paste (wt.-%) | Catalyst (wt.-%) |
|---|---|---|
| Vinyl-terminated polydimethysiloxane | 40.8 | 50.0 |
| Pigment | 2.2 | — |
| Surfactant | 0.9 | — |
| Silicone oil | 14.2 | 15.0 |
| Poly(methyl)(hydrogen)siloxane | 7.9 | — |
| Pyrogenic Silica (Aerosil R 202) | 0.7 | 1.0 |

-continued

| Component | Base paste (wt.-%) | Catalyst (wt.-%) |
|---|---|---|
| Glass Beads (K37), d50/μm: 40 μm | 33.3 | 33.0 |
| Platinum - solution | — | 1 |

The compositions were investigated with regard to tensile strength, consistency and Shore A hardness. The values are given in Table 2.

Typically, the compositions started to cure after about 40 to about 120 s and were set after about 2.5 to about 4.5 min at 23° C.

The results were compared with a commercially available VPS material used for precision impressions (Express™ 2 Light Body Flow; 3M ESPE), to a commercially available alginate replacement VPS material (Position™ Penta; 3M ESPE), and to a commercially available Alginate impression material (Palgat Plus Quick; 3M ESPE).

TABLE 2

| Composition | Consistency [mm] | Tensile strength [MPa] | Shore A hardness (24 h) |
|---|---|---|---|
| Express ™ 2 Light Body Flow | 44 | 4.5 | 54 |
| Position ™ Penta | 36 | 1.2 | 48 |
| Palgat ™ Plus Quick | 32 | 0.7 | 29* |
| Example 1 | 40 | 0.51 | 37 |
| Example 2 | 50 | 0.71 | 36 |
| Example 3 | 52 | 1.01 | 35 |
| Example 4 | 37 | 0.6 | 41 |
| Example 5 | 38 | 0.4 | 33 |

*stored in a hygrophor.

As can be seen, the properties of the compositions according to Examples 1 to 5 are different compared to e.g. the Express™ 2 Light Body Flow material (precision VPS material) and are much closer to the properties of the Palgat™ Plus Quick material (Alginate).

The invention claimed is:

1. A dental impression composition comprising a hardenable matrix and glass beads having a particle size (d50/μm) equal to or below about 60 μm, and a tensile strength (according to DIN 53504), after hardening, of up to about 1 MPa, wherein the composition is characterized by the following parameter: a setting time within about 15 min after mixing at ambient conditions.

2. The dental composition of claim 1, wherein the glass beads are present in an amount of up to about 80 wt.-% with respect to the weight of the whole composition.

3. The dental composition of claim 1, wherein the composition is characterized by the following parameter:
a consistency (according to ISO 4823) of 0, 1, 2 or 3.

4. The dental composition of claim 1, wherein in the composition, after curing, is characterized by an elongation at break (according to DIN 53504) of about 10 to about 300%.

5. The dental composition of claim 1, wherein the hardenable matrix comprises moieties selected from polyether, polyester, polyurethane and/or siloxane moieties or mixtures of two or more of these moieties.

6. The dental composition of claim 1, wherein the glass beads are characterized by hollow interiors.

7. The dental composition of claim 1 further comprising a filler being different from the glass beads.

8. A dental impression composition comprising:
at least one polydimethylsiloxane with at least 2 aliphatically unsaturated groups as component (A),
at least one SiH compound with ≥2 SiH-groups per molecule, as component (B),
a catalyst as component (C) being able to catalyse the reaction between components (A) and (B),
glass beads as component (D) particle size (d50/μm) equal or below about 60 μm,
optionally at least one non-reactive polydimethylsiloxane as component (E),
optionally fillers as component (F) being different from the glass beads,
optionally surfactants or wetting agents as component (G),
optionally further additives as component (H) selected from the group consisting retarders, rheology modifiers, inhibitors, pigments, plasticizers, dyes, pigments, odorous substances, flavourings, hydrogen scavenger alone or in admixture
wherein the composition has, after hardening, a tensile strength (according to DIN 53504) of up to about 1 MPa, and
wherein the composition is characterized by the following parameter: a setting time within about 15 min after mixing at ambient conditions.

9. The dental composition of claim 8, wherein the components are present in the following amounts:
Component (A): from about 20 wt.-% to about 60 wt.-%,
Component (B): from about 0.1 wt.-% to about 15 wt.-%,
Component (C): from about 0.001 wt.-% to about 0.1 wt.-%,
Component (D): from about 0.5 wt.-% to about 70 wt.-%,
Component (E): from about 0 wt.-% to about 30 wt.-%,
Component (F): from about 0 wt.-% to about 75 wt.-%,
Component (G): from about 0 wt.-% to about 10 wt.-%,
Component (H): from about 0 wt.-% to about 10 wt.-%,
wt.-% with respect to the whole composition.

10. A kit of parts comprising a base paste and a catalyst paste separated from each other before use, wherein the base paste comprises components (A) and (B) and the catalyst paste comprises component (C) or (C) and (A), and wherein component (D) and the other optional components (E), (F), (G) and (H) can be present either in the base paste or the catalyst paste or the base paste and the catalyst paste, wherein components (A) to (H) are as described in any of claim 8 or 9,
wherein the kit is characterized by the following parameter: a setting time within about 15 min after mixing the base paste and the catalyst paste at ambient conditions, and
wherein the mixed composition has, after hardening, a tensile strength (according to DIN 53504) of up to about 1 MPa.

11. A method of producing a dental composition according to claim 8 comprising the step of combining glass beads having a particle size (d50/μm) equal to or below about 60 μm with a composition comprising components (A), (B), (C), wherein components (A), (B) and (C) are as described in any of claim 8 or 9.

12. A method of preparing a dental impression composition according to claim 1 comprising combining glass beads with a hardenable matrix, wherein the glass beads have a particle size (d50/μm) equal or below about 60 μm and wherein the composition, after hardening, has a tensile strength (according to DIN 53504) of up to about 1 MPa.

13. A method of taking a dental impression comprising hardening a dental impression composition as described in claim 1.

14. A method of taking a dental impression comprising hardening a composition comprising an alginate containing dental impression composition having the alginate substituted with the dental impression composition as described in any of claim 1 or 8.

15. A method of taking a dental impression comprising hardening a dental impression composition as described in claim 8.

16. The dental composition of claim 4, wherein in the composition, after curing, is characterized by an elongation at break (according to DIN 53504) of about 15 to about 200%.

17. The dental composition of claim 1, wherein in the composition, after curing, is characterized by a shore A hardness (according to DIN 53505) of about 10 to about 75.

18. The dental composition of claim 17, wherein in the composition, after curing, is characterized by a shore A hardness (according to DIN 53505) of about 30 to about 50.

19. The dental composition of claim 1, wherein the composition, after curing, is characterized by a density (according to the Archimedes method) of about 0.4 to about 1.8 g/ml.

20. The dental composition of claim 1, wherein the composition is characterized a consistency (according to ISO 4823) of 2.

21. The dental composition of claim 1, wherein the glass beads have a particle size (d50/μm) equal to or below about 50 μm.

22. The dental composition of claim 1, wherein the glass beads are characterized by a density from about 0.10 to about 0.70 g/ml.

23. The dental composition of claim 1, wherein the glass beads are characterized by an impact strength greater than or equal to about 1.7 MPa.

24. The dental composition of claim 8, wherein in the composition, after curing, is characterized by an elongation at break (according to DIN 53504) of about 10 to about 300%.

25. The dental composition of claim 24, wherein in the composition, after curing, is characterized by an elongation at break (according to DIN 53504) of about 15 to about 200%.

26. The dental composition of claim 8, wherein in the composition, after curing, is characterized by a shore A hardness (according to DIN 53505) of about 10 to about 75.

27. The dental composition of claim 26, wherein in the composition, after curing, is characterized by a shore A hardness (according to DIN 53505) of about 30 to about 50.

28. The dental composition of claim 8, wherein the composition, after curing, is characterized by a density (according to the Archimedes method) of about 0.4 to about 1.8 g/ml.

29. The dental composition of claim 8, wherein the composition is characterized a consistency (according to ISO 4823) of 2.

30. The dental composition of claim 8, wherein the glass beads have a particle size (d50/μm) equal to or below about 50 μm.

31. The dental composition of claim 8, wherein the glass beads are characterized by hollow interiors.

32. The dental composition of claim 8, wherein the glass beads are characterized by a density from about 0.10 to about 0.70 g/ml.

33. The dental composition of claim 8, wherein the glass beads are characterized by an impact strength greater than or equal to about 1.7 MPa.

34. The method of claim 13, wherein the hardened dental impression composition is in the form of a mould and the mould is filled with a crown or bridge material.

35. The method of claim 15, wherein the hardened dental impression composition is in the form of a mould and the mould is filled with a crown or bridge material.

\* \* \* \* \*